United States Patent
Haddon et al.

(10) Patent No.: US 8,592,612 B1
(45) Date of Patent: Nov. 26, 2013

(54) WATER SOLUBLE CARBON NANOTUBES

(75) Inventors: Robert C. Haddon, Riverside, CA (US); Irina Kalinina, Riverside, CA (US); Elena Bekyarova, Riverside, CA (US)

(73) Assignee: Carbon Solutions, Inc., Riverside, CA (US)

( * ) Notice: Subject to any disclaimer, the term of this patent is extended or adjusted under 35 U.S.C. 154(b) by 142 days.

(21) Appl. No.: 13/087,306

(22) Filed: Apr. 14, 2011

Related U.S. Application Data

(60) Provisional application No. 61/324,146, filed on Apr. 14, 2010.

(51) Int. Cl.
*C07D 307/12* (2006.01)

(52) U.S. Cl.
USPC ............................................ 549/501

(58) Field of Classification Search
USPC ............................................ 549/501
See application file for complete search history.

(56) References Cited

PUBLICATIONS

Hu, H. et al., "Nitric Acid Purification of Single-Walled Carbon Nanotubes," J. Phys. Chem. B 2003, vol. 107, pp. 13838-13842.
Itkis, M. E. et al., "Purity Evaluation of As-Prepared Single-Walled Carbon Nanotube Soot by Use of Solution Phase Near-IR Spectroscopy," Nano Lett. 2003, vol. 3, pp. 309-314.
Liu, J. et al., "Fullerene Pipes," Science 1998, vol. 280, pp. 1253-1255.
Yu, A. et al., "Application of Centrifugation to the Large-Scale Purification of Electric Arc Produced Single-Walled Carbon Nanotubes," J. Am. Chem. Soc. 2006, vol. 128, pp. 9902-9908.
Zhao, B., et al., "Synthesis and Characterization of Water Soluble Single-Walled Carbon Nanotube Graft Copolymers," J. Am. Chem. Soc., 2005, vol. 127, pp. 8197-8203.

*Primary Examiner* — Taofiq A Solola
(74) *Attorney, Agent, or Firm* — Knobbe, Martens, Olson & Bear, LLP

(57) ABSTRACT

Embodiments of the present disclosure present systems and methods for the synthesis of carbon nanotubes (CNTs) functionalized with mono-terminated, protected polyethylene glycol (PEG). As compared with bi-functional PEG, mono-terminated PEG the PEG-THFF oligomer has only one reaction site. The use of mono-terminated PEG may enhance the solubility of CNTs functionalized with mono-terminated PEG by inhibiting cross-linking between nanotubes and leads to a dramatic increase in aqueous solubility. In an example, single-walled carbon nanotubes functionalized with PEG having a tetrahydrofurfuryl (THFF) terminal group (SWNT-PEG-THFF) is found to disperse in water by ultrasonication and forms stable viscous dispersions at concentrations as high as about 9 g/L. This result exceeds the solubility of a previously reported SWNT-PEG graft copolymer, approximately 6 g/L, by more than 30%.

20 Claims, 9 Drawing Sheets

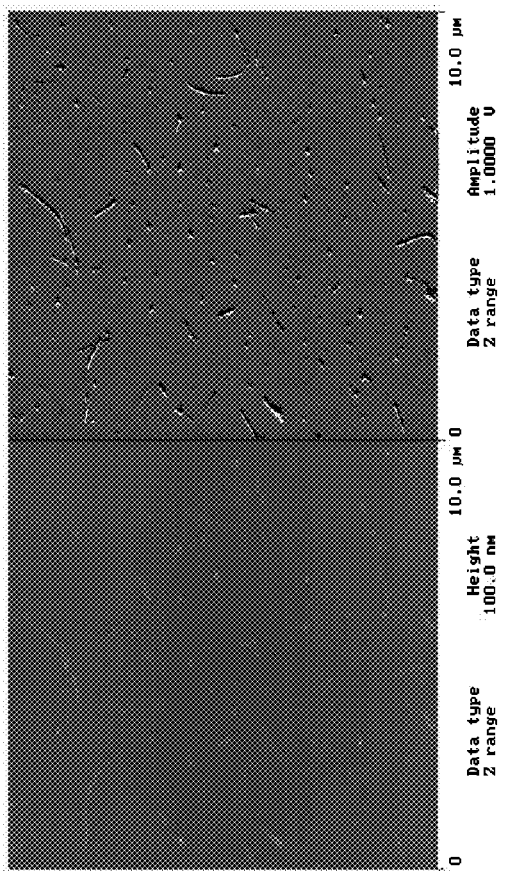
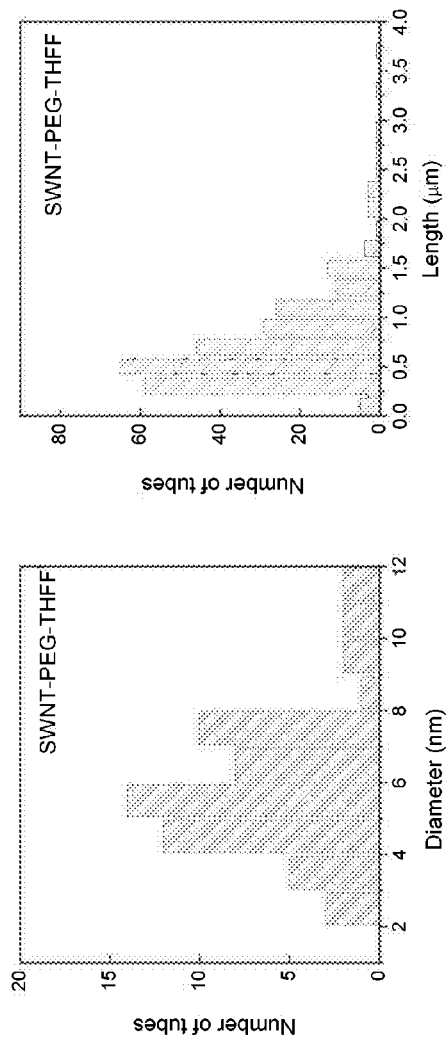
FIG. 7A
FIG. 7B
FIG. 7C

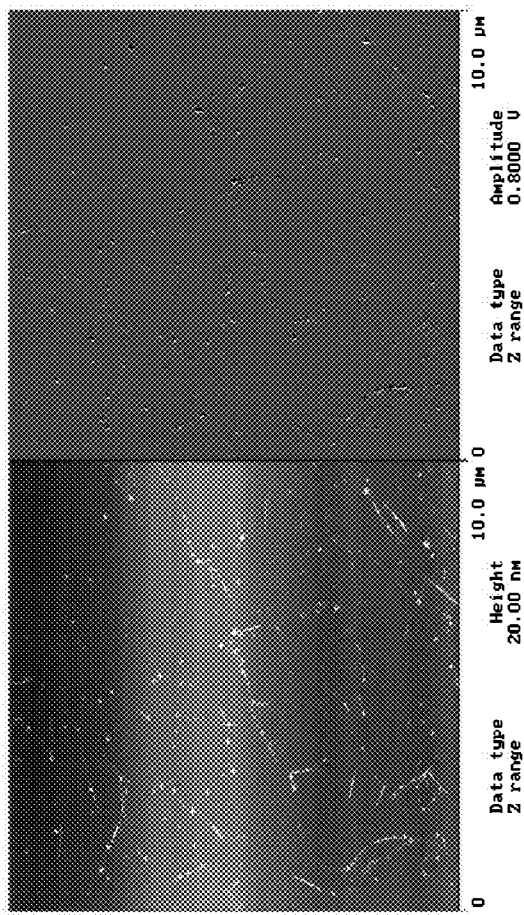
FIG. 8A
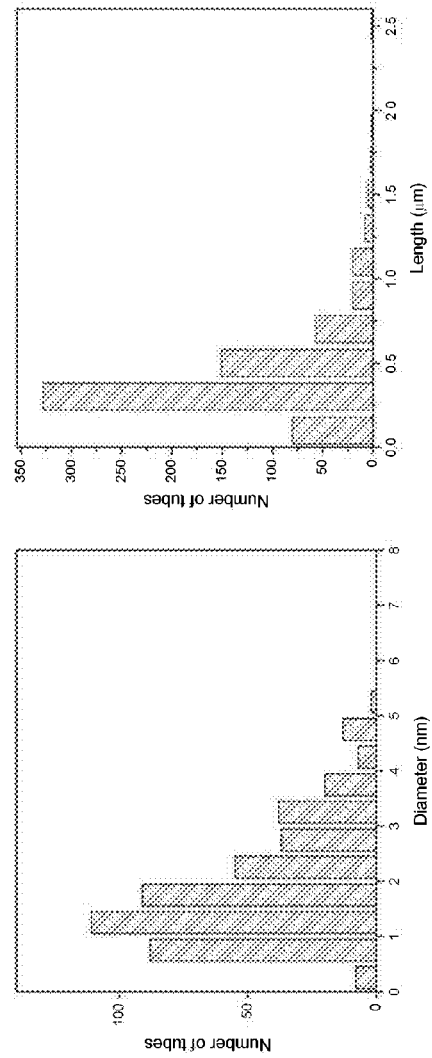
FIG. 8C
FIG. 8B

WATER SOLUBLE CARBON NANOTUBES

CROSS-REFERENCE TO RELATED APPLICATIONS

This application claims the benefit of priority under 35 U.S.C. §119(e) of U.S. Provisional Application No. 61/324,146, filed on Apr. 14, 2010 and entitled, "WATER SOLUBLE CARBON NANOTUBE—TETRAHYDROFURFURY—POLYETHETHYLENE GLYCOL GRAFT COPOLYMERS." The entirety of this application is incorporated herein by reference.

STATEMENT REGARDING FEDERALLY SPONSORED R&D

Embodiments of the present disclosure were made with Government support under Contract Number H94003-04-02-0404-P00002 awarded by Department of Defense (DOD/DMEA-CNN). The Government has certain rights in this invention.

BACKGROUND

1. Field

Embodiments of the present disclosure pertain to functionalized carbon nanotubes and, in particular, to functionalization of carbon nanotubes with mono-terminated, protected polyethylene glycol (PEG)

2. Description of the Related Art

Carbon nanotubes (CNTs) have inert chemical structure because they are comprised of $sp^2$-bonded carbon atoms. Many applications, including composite materials, conductive and transparent thin films, electronics, sensors, and biomedicine, rely on the ability to process the CNTs.

Stable suspensions of CNTs, such as single walled carbon nanotubes (SWNTs), have been achieved in water with the use of surfactants, DNA, and non-covalent and covalent attachment of polymers. Covalent functionalization is a valuable approach to the preparation of CNT materials, as controlled compositions and reproducible properties may be obtained.

SUMMARY

In an embodiment, a method of forming water-soluble carbon nanotubes (CNTs) is provided. The method comprises providing carbon nanotubes (CNTs) functionalized with carboxylic acid (CNT-COOH). The method further comprises reacting the carboxylic acid functionalized carbon nanotubes (CNT-COOH) with a reactant to form an intermediate reaction product. In an embodiment, the intermediate reaction product may comprise carbon nanotubes functionalized with COCl (CNT-COCl). In another embodiment, the intermediate reaction product may comprise carbon nanotubes functionalized with a group of the form

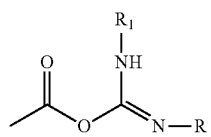

where R and $R_1$ are selected from phenyl, $C_3H_7$, $C_3H_6N(CH_3)_2$, and $C_2H_5$. The method may further comprise reacting the intermediate product with a mono-terminated, protected-polyethylene glycol (PEG) oligomer to form a carbon nanotube functionalized with the mono-terminated, protected PEG oligomer (CNT-PEG-T).

In another embodiment, a water-soluble carbon nanotube is provided. The water-soluble carbon nanotube comprises a carbon nanotube functionalized with a mono-terminated, protected-polyethylene glycol (CNT-PEG-T).

In a further embodiment, a water-soluble carbon nanotube is provided. The water-soluble carbon nanotube may comprise a structure of the form:

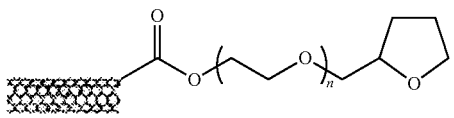

where n is between 2 to 20 and ▨▨▨▨ represents a carbon nanotube.

BRIEF DESCRIPTION OF THE DRAWINGS

FIG. 7A is an atomic force microscope (AFM) image of an embodiment of SWNT-PEG-THFF dispersed in water by ultrasonication. The approximately spherical particles illustrated in FIG. 7A originate from the solvent;

FIGS. 7B-7C presents histograms of the diameter and length distributions, respectively, of SWNT-PEG-THFF measured from the image of FIG. 7A;

FIG. 8A is an atomic force microscope (AFM) image of an embodiment of SWNT-PEG-THFF dispersed in water by ultrasonication and high shear mixing. The approximately spherical particles illustrated in FIG. 7A originate from the solvent; and FIGS. 8B-8C presents histograms of the diameter and length distributions, respectively, of SWNT-PEG-THFF measured from the image of FIG. 8A.

DETAILED DESCRIPTION

The terms "approximately", "about", and "substantially" as used herein represent an amount equal to or close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

Embodiments of the present disclosure present systems and methods for the synthesis of CNT-PEG compounds that improve the water solubility of the CNTs. The CNT-PEG compounds are formed by covalent functionalization of CNTs with mono-terminated PEG. Examples of the PEG terminal group may include, but are not limited to, tetrahydrofurfuryl (THFF), alkyl-tetrahydrofurfuryl, alkyl-vinyl, alkyl, alkene, and aryl functional groups. While embodiments of the disclosure may be discussed below in the context of THFF, however one or more of the above terminal groups may be alternatively employed without limit.

As compared with bi-functional PEG, mono-terminated PEG possesses a single reaction site. The use of mono-terminated PEG may, therefore, enhance the solubility of CNT-PEG graft copolymers by inhibiting cross-linking between the CNTs. Cross-linking can occur in case of covalent bonding of CNT-COOH to bi-functional PEG, which has reactive OH-groups terminating both ends of the oligomer chain. Furthermore, the functionalization of CNTs with mono-terminated PEG having very short chain (e.g., MW on the order of 200) leads to increased CNT content in the final graft copolymer. It may be understood, however, that mono-terminated PEGs having MW greater than about 200 or lower than about 200 may also be employed without limit.

CNT graft copolymers formed by covalent functionalization with mono-terminated PEG, SWNT-PEG-THFF graft copolymers were synthesized and characterized using TGA, near-IR, and mid-IR spectroscopy and AFM to examine the water solubility of these compounds. Beneficially, it is observed that a SWNT-PEG-THFF material disperses in water by ultrasonication and forms stable, viscous dispersions at concentrations as high as about 9 g/L, exceeding the solubility of a previously reported SWNT-PEG graft copolymer, approximately 6 g/L, by more than 30%.

Figure 1:
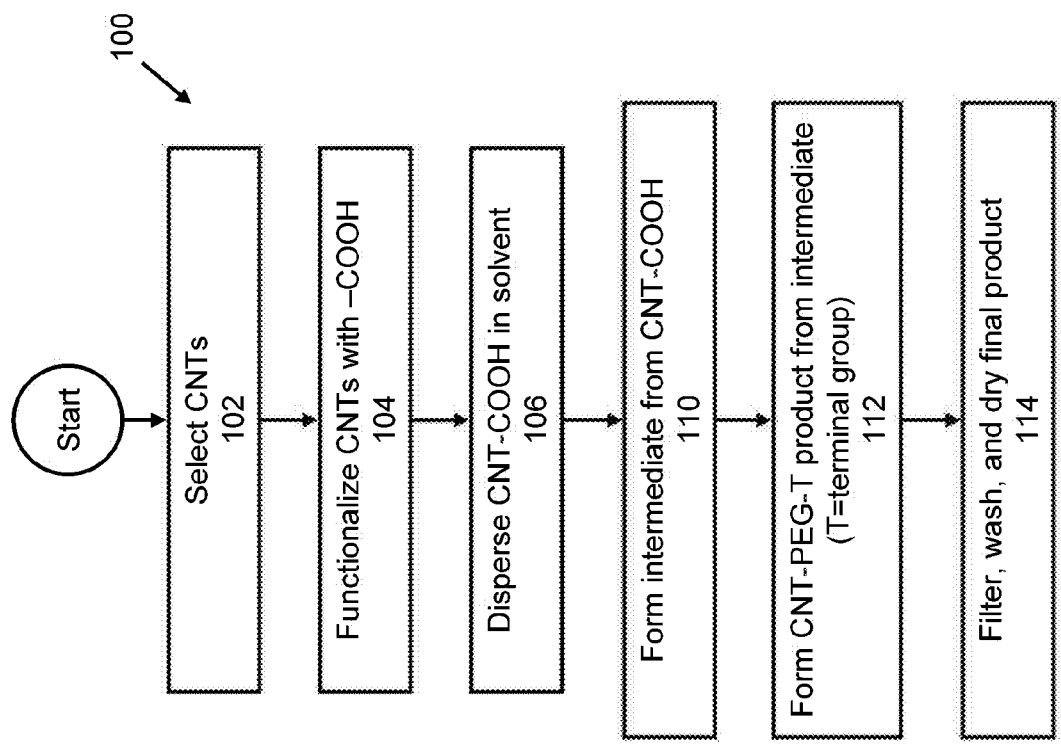
FIG. 1 is a flow diagram of one embodiment of a process for the functionalization of carboxylic acid-terminated carbon nanotubes (CNT-COOH) with mono-terminated polyethylene glycol (PEG)
Figure 2:
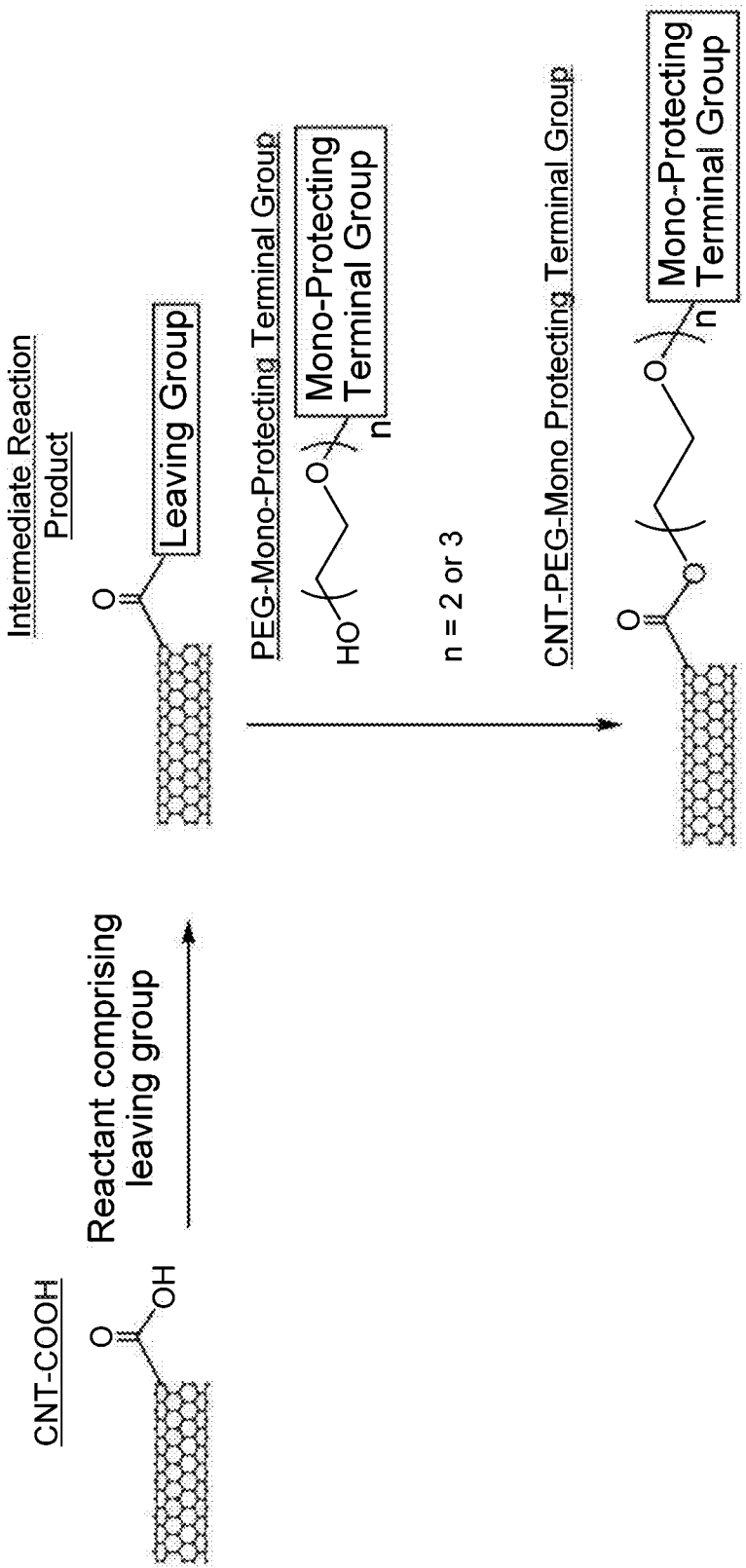
FIG. 2 is a schematic reaction illustrating an embodiment of the functionalization of carboxylic acid-terminated carbon nanotubes (CNT-COOH) with mono-terminated polyethylene glycol (PEG)

An embodiment of a synthetic process 100 for formation of CNT graft copolymers functionalized with mono-terminated PEG is schematically illustrated in FIG. 1. The method 100 begins with selection of carbon nanotube materials in block 102. Embodiments of the CNTs may include, but are not limited to, single-walled carbon nanotubes (SWNTs), double-walled carbon nanotubes (DWNTs), few walled carbon nanotubes (FWNTs), and multi-walled carbon nanotubes (MWNTs). In embodiments discussed below, reference may be made to SWNTs. One of skill art may understand, however, that embodiments of the disclosure may be employed with other forms of carbon nanotubes without limit.

In one embodiment, the CNTs may comprise SWNTs. The SWNTs, in one embodiment, may be electric arc produced. In alternative embodiments, the SWNTs may be formed by chemical vapor deposition. In further embodiments, the SWNTs may be formed by laser ablation. In other embodiments, the SWNTs may be produced through a high-pressure carbon monoxide process (HiPco).

The geometry of the SWNTs formed may also be varied, as necessary. In one embodiment, the diameter of the SWNT bundles may vary within the range between about 1 mm to about 5 nm. In other embodiments, the length of the SWNTs may vary within the range between about 50 nm to about 5 μm.

In block 104, the selected CNTs may be further functionalized with carboxylic acid groups (—COOH). In one embodiment, the carboxylic acid functionalization may be performed by treatment of the CNTs with nitric acid according to Hu, H.; Zhao, B.; Itkis, M. E.; Haddon, R. C., Nitric Acid Purification of Single-Walled Carbon Nanotubes. *J. Phys. Chem. B* 2003, 107, 13838-13842. and/or Yu, A.; Bekyarova, E.; Itkis, M. E.; Fakhrutdinov, D.; Webster, R.; Haddon, R. C., Application of Centrifugation to the Large-Scale Purification of Electric Arc Produced Single-Walled Carbon Nanotubes. *J. Am. Chem. Soc.* 2006, 128, 9902-9908, each of which is incorporated by reference in its entirety. In another embodiment, the carboxylic acid functionalization may be performed by treatment of the CNTs with a mixture of nitric and sulfuric acid according to Liu, J.; Rinzler, A. G.; Dai, H.; Hafner, J. H.; Bradley, R. K.; Boul, P. J.; Lu, A.; Iverson, T.; Shelimov, K.; Huffman, C. B.; Rodriguez-Macias, F.; Shon, Y.-S.; Lee, T. R.; Colbert, D. T.; Smalley, R. E., Fullerene Pipes. *Science* 1998, 280, 1253-1255 which is incorporated by reference in its entirety.

In block 106, the carboxylic acid functionalized CNTs (CNT-COOH) may be dispersed in a solvent. Examples of the solvent may include, but are not limited to, dimethylformamide (DMF) and dimethylacetamide. Dispersion of the CNT-COOH may be performed by ultrasonication, high shear mixing, and combinations thereof. The CNT-COOH may be added to the solvent in concentrations within the range between about 0.2 g/L to about 5 g/L. Ultrasonication may be performed in the solvent at a sonic power within the range between about 75 W to about 270 W for a time within the range between about 30 min to about 20 h. High shear mixing may be performed for a duration within the range between about 30 min to about 3 h in order to obtain a substantially homogeneous dispersion.

In block 110, the dispersed CNT-COOH material may be reacted with at least one reactant possessing a leaving group in order to form an intermediate product. The intermediate product may comprise the CNT and the leaving group. The intermediate product may be represented by the form:

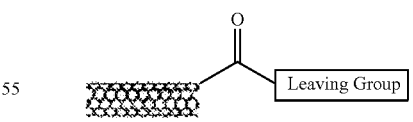

where the CNT is represented by 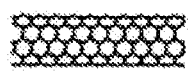. This intermediate product enables relatively easy attachment of the mono-terminated PEG to the CNT. For example, such attachment may be accomplished by reacting the intermediate product with a mono-terminated, protected PEG oligomer.

In one embodiment, the leaving group may comprise chlorine (Cl) and the intermediate product may be of the form:

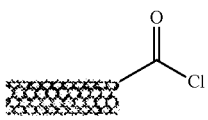

Embodiments of first reactants which may react with CNT-COOH to form an intermediate comprising a Cl leaving group (e.g., COCl) may include, but are not limited to, oxalyl chloride, thionyl chloride, phosphorus trichloride, or phosphorus pentachloride. In an embodiment, the concentrations of the first reactant and CNT-COOH may vary within the range between about 10 mL/L to about 100 mL/L and about 0.2 g/L to about 5 g/L, respectively. In another embodiment, the reaction may be carried out with powder of CNT-COOH and DMF may be added as a catalyst at a concentration within the range between about 0.01 L/g to about 10 L/g.

In another embodiment, the carboxylic acid groups in CNTs may be activated with carbodiimides and the leaving group may comprise acylisourea. The intermediate product may be of the form:

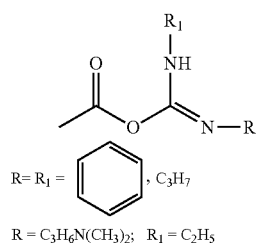

Embodiments of second reactants which may react with CNT-COOH to form an intermediate comprising an

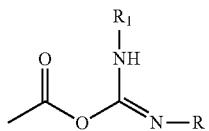

leaving group may include, but are not limited to one or more of N,N'-dicyclohexylcarbodiimide (DCC), N,N'-diisopropylcarbodiimide (DIC), and 1-ethyl-3-(3-dimethylaminopropyl)carbodiimide (EDC).

N,N'-dicyclohexylcarbodiimide (DCC) and N,N'-diisopropylcarbodiimide (DIC) may be used in organic solvents and 1-ethyl-3-(3-dimethylaminopropyl)carbodiimide (EDC) may be used in aqueous solutions to form the above intermediate product. Additives, including, but not limited to, N-hydroxysuccinimide, may be added to facilitate reaction with mono-terminated, protected PEG (e.g., PEG-THFF) and increase the yield. In an embodiment, the concentrations of the second reactant and CNT-COOH may vary within the range between about 3 g/L to about 20 g/L and about 0.5 g/L to about 5 g/L, respectively.

Prior to addition of the reactant comprising the leaving group, the dispersed CNT-COOH may be flushed with an inert gas (e.g., argon, nitrogen and the like) for a selected duration and cooled. The presence of the inert gas may assist in removal of water from the system and may inhibit vigorous reaction between the reactant possessing the leaving group and the CNT-COOH. For example, the dispersed CNT-COOH may be flushed with the inert gas for a time duration within the range between about 1 to about 24 hours and cooled to a temperature within the range between about −10° C. to about 10° C.

The reactant comprising the leaving group may be added to the CNT-COOH material while under the inert gas and the reaction mixture may be stirred at one or more temperatures for selected time periods. In one embodiment, the reaction mixture may be stirred at a temperature of about 0° C. for a time duration within the range between about 1 h to about 5 h, then heated to about room temperature and stirred for a time duration within the range between about 1 h to about 3 hrs.

Subsequently, an excess amount of the reactant possessing the leaving group may be removed. For example, the vessel containing the reaction mixture may be heated to a temperature greater than the boiling point of the reactant for a time duration within the range between about 12 h to about 24 h to substantially remove excess reactant. This process yields the intermediate reaction product possessing the leaving group.

In block 112, the intermediate product may be reacted with the mono-terminated PEG to form a CNT graft copolymer functionalized with the mono-terminated, protected PEG (CNT-PEG-T). In certain embodiments, the terminal group may comprise tetrahydrofurfuryl (THFF), alkyl-tetrahydrofurfuryl, alkyl-vinyl, alkyl, alkene, and aryl functional groups. The mono-terminated PEG oligomer may be provided in a concentration ranging between about 6 g/L to 60 g/L.

The mixture may also be heated and stirred to facilitate the reaction. In one embodiment, the mixture may be heated to a temperature within the range between about 100° C. to about 130° C. for a time duration within the range between about 1 h to 10 days. Stirring of the mixture may be performed before and/or during at least a portion of the heating process.

After cooling the mixture to about room temperature, the mixture may be filtered, washed, and dried in block 114 to yield the final product. For example, the mixture may be washed with a solvent repeatedly until the filtrate is approximately clear. The filter may comprise a membrane having a pore sizes within the range between about 0.2 μm to about 1 μm. Examples of the washing solvent may include, but are not limited to, anhydrous N,N,-dimethylformamide (DMF), ethanol, acetone, and water. The resulting product may be subsequently dried under vacuum or in air. In certain embodiments, the loading fraction of CNTs within the CNT-PEG-T product may vary within the range between about 50 wt. % to about 90 wt. %. The resulting product may be further exfoliated by one or more of ultrasonication for a time duration within the range between about 2 h to 10 h and high shear mixing for a time duration within the range between about 30 min to about 5 h.

In an embodiment, the above described process may be employed to fabricate CNT-PEG-T materials comprising single walled carbon nanotubes and THFF (SWNT-PEG-THFF). A dispersion of about 0.1 to about 10 g/L of carboxylic acid functionalized SWNT material (SWNT-COOH) in anhydrous dimethylformamide (DMF) may be prepared by ultrasonication at a sonic power within the range between about 75 W to about 270 W for a time duration within the range between about 30 min to about 5 h and then high-shear mixing for a time duration within the range between about 30 min to about 3 h.

The reaction vessel may be further connected to a condenser, flushed with an inert gas, such as argon, for a time duration within the range between about 1 h to about 3 h, and then immersed in an ice bath to reduce the temperature of the SWNT material to within the range between approximately −5° C. to about 5° C.

Subsequently, about 10 mL/L to about 100 mL/L of oxalyl chloride may be added, dropwise, to the SWNT-COOH dispersion under the inert gas. The reaction mixture may be stirred at a temperature of about 0° C. for a time duration within the range between about 1 h to about 5 h, heated to about room temperature, and stirred for a further time duration within the range between of about 1 h to about 3 h. The reaction vessel may then be substantially immersed in an oil bath and heated to a temperature greater than the boiling point of oxalyl. chloride (about 63° C.) for a time duration within the range between about 12 to 24 hours in order to substantially remove excess oxalyl chloride. This process may yield an intermediate reaction product of SWNT-COCl.

In an example, about 6 g/L to about 60 g/L of PEG-THFF may be added to the SWNT-COCl intermediate reaction product. The mixture may be heated at a temperature within the range between about 100° C. to about 130° C. for a time duration within the range between about 3 to 10 days. Stirring of the PEG-THFF/SWNT-COCl may be performed before and/or during at least a portion of the heating process. In certain embodiments, the carboxylic acid groups of the SWNTs may undergo substantially complete covalent functionalization with the PEG oligomer. For example, the degree of covalent functionalization may exceed approximately 80%, approximately 85%, approximately 90%, approximately 95%, approximately 97%, and approximately 99%.

After cooling to about room temperature, the mixture may be filtered through a membrane having a pore sizes within the range between about 0.2 μm to about 1 μm and washed with DMF and distilled water repeatedly until the filtrate is clear. The resulting SWNT-PEG-THFF product may be subsequently dried under vacuum. In certain embodiments, the loading of SWNTs within the SWNT-PEG-THFF product may range between about 50 wt. % to about 90 wt. %.

EXAMPLES

In the following examples, the synthesis and characterization of embodiments of SWNT-PEG-THFF graft copolymers are discussed in greater detail. In particular, a number of tests are performed in order to characterize a SWNT-COOH starting product and a SWNT-PEG-THFF graft copolymer final product. Such characterization may include, but is not limited to, carboxylic acid content of the SWNT-COOH starting product, atomic force microscopy (AFM) to examine selected geometric characteristics of the starting and final products (e.g., length, diameter), infrared spectroscopy to examine bond formation in the starting and final products, thermogravimetric analysis to examine the PEG-THFF loading of the functionalized SWNTs, the loading of SWNTs within the SWNT-PEG-THFF product, solubility of the SWNT-PEG-THFF product, and dispersibility of the SWNT-PEG-THFF product. The examples highlight that the SWNT-PEG-THFF materials may be synthesized through the above described routes and exhibit high solubility and dispersibility in water. It may be understood, however, that these examples are discussed for illustrative purposes and should not be construed to limit the disclosed embodiments.

In an embodiment, purified SWNTs having carboxylic acid functionality (SWNT-COOH, P3-SWNT—Carbon Solutions, Riverside, Calif.) were employed in embodiments of the SWNT-PEG-THFF synthesis. The SWNT materials were prepared by electric-arc discharge. The SWNTs further possessed a metal residue of about 5.4 wt. % and a relative carbonaceous purity of about 115%, as estimated by solution-phase near-IR spectroscopy against reference R2 according to the method of Itkis, M. E.; Perea, D.; Niyogi, S.; Rickard, S.; Hamon, M.; Hu, H.; Zhao, B.; Haddon, R. C., Purity Evaluation of As-Prepared Single-Walled Carbon Nanotube Soot by Use of Solution Phase Near-IR Spectroscopy. *Nano Lett.* 2003, 3, 309-314, the entirety of which is hereby incorporated by reference. Reagents of oxalyl chloride and polyethylene glycol tetrahydrofurfuryl ether (PEG-THFF, MW of approximately 200) were purchased from Aldrich and anhydrous N,N-dimethylformamide (DMF) was purchased from EMD Chemicals Inc. The functionalization reactions were performed under argon, using oven-dried glassware. Sodium bicarbonate (ACS grade) was purchased from Fisher Scientific, and 0.05 N HCl and 0.05 N NaOH were obtained from RICCA Chemicals.

Example 1

Synthesis of SWNT-PEG-THFF Graft Copolymer

Figure 3:
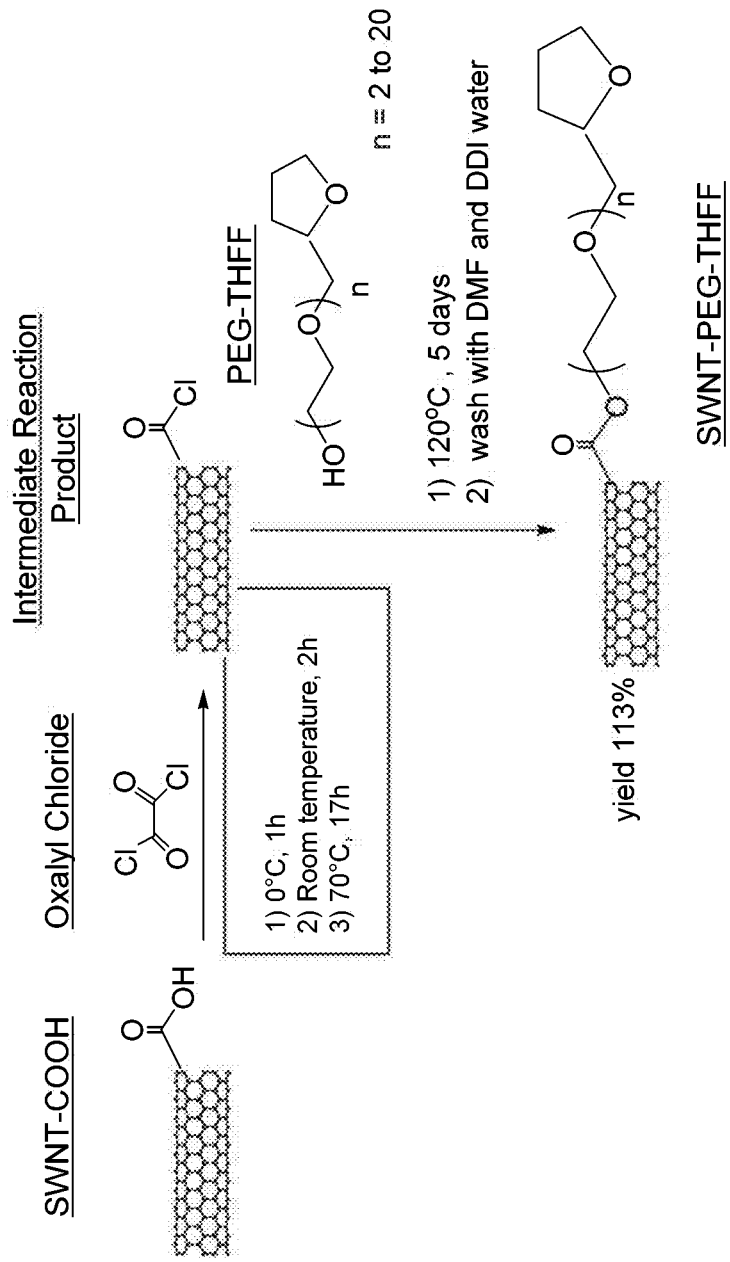
FIG. 3 is a schematic reaction illustrating an embodiment of the functionalization of carboxylic acid-terminated single walled carbon nanotubes (SWNT-COOH) with tetrahydrofurfuryl terminated poly-ethylene glycol (PEG-THFF)

An embodiment of a synthetic process for the formation of SWNT-PEG-THFF is schematically illustrated in FIG. 3. About 1 g of SWNT-COOH material (P3-SWNT) was dispersed in about 1 L of anhydrous dimethylformamide (DMF) by ultrasonication for about 2 h, followed by high-shear mixing for about 1 h. The vessel containing the dispersion was subsequently connected to a condenser, flushed with argon for a time duration within the range between about 1 h to about 3 h, and immersed in an ice bath to lower the temperature of the dispersion to about 0° C.

To form the intermediate SWNT-COCl product, about 20 mL oxalyl chloride was added dropwise to the SWNT dispersion at a temperature of about 0° C. under argon. The reaction mixture was then stirred at a temperature of about 0° C. for about 1 h, heated to about room temperature, and further stirred for about 2 h. The flask containing the dispersion was then immersed in an oil bath and heated to about 70° C. overnight (e.g., about 17 h) to remove the excess oxalyl chloride, which has a boiling point of about 63° C. This process yielded the intermediate reaction product of SWNT-COCl.

To form the final product of SWNT-PEG-THFF, about 12 mg of PEG-THFF was added at about room temperature to the intermediate product and the mixture was heated at about 120° C. for about 5 days. After cooling to about room temperature, the mixture was filtered through an approximately 0.22-μm Teflon membrane and washed approximately 2 to 5 times with DMF and distilled water. The product was dried under vacuum to yield a black solid of SWNT-PEG-THFF.

Example 2

IR-Characterization of Ester Bond Formation Between SWNTs and PEG

Ester bond formation between the SWNTs and PEG chain was confirmed by mid-infrared (mid-IR) spectroscopy. Mid-IR spectra were measured using a Nicolet Nexus 670 FI-IR at about 4 or 8 cm$^{-1}$ resolution in the frequency range between about 400 cm$^{-1}$ to about 4000 cm$^{-1}$. Aqueous dispersions were used to prepare thin films on ZnSe substrates for characterization.

Figure 4:
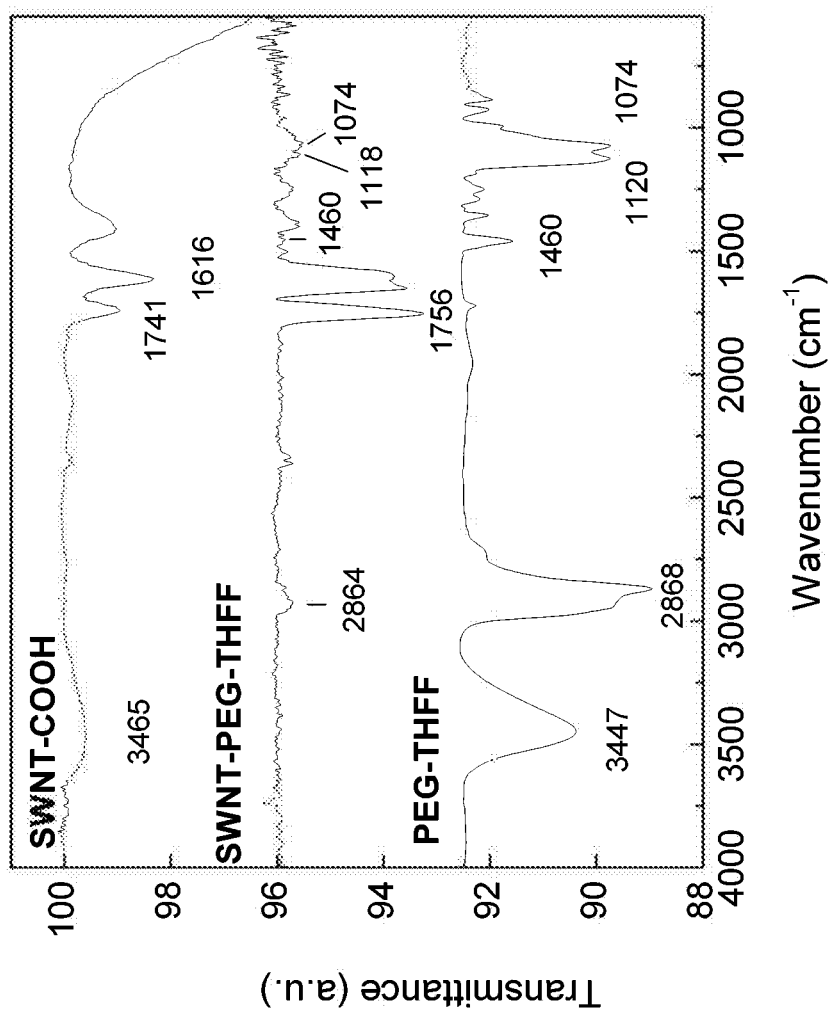
FIG. 4 presents Fourier transform-infrared (FT-IR) spectra of embodiments of films of SWNT-COOH, PEG-THFF, and SWNT-PEG-THFF.

FIG. 4 illustrates the spectra measured for embodiments of neat PEG-THFF, SWNT-COOH, and SWNT-PEG-THFF materials. The IR spectrum of the SWNT-COOH shows a broad peak at about 1741 cm$^{-1}$, which may be attributed to the C═O stretching vibration of the carboxylic acid groups. In the functionalized SWNT-PEG-THFF graft copolymer, the C=O stretch is shifted to about 1756 cm$^{-1}$, due to the formation of an ester bond. In addition, the OH stretching vibration, which appears at about 3447 cm$^{-1}$ in the spectra of PEG-THFF, is not present in the spectrum of the SWNT-PEG-THFF material. The peaks at about 2868 cm$^{-1}$ (PEG-THFF) and 2864 cm$^{-1}$ (SWNT-PEG-THFF) are due to C—H stretch vibrations. The deformation vibration of the CH$_2$ group shows a peak at about 1464 cm$^{-1}$, which in the spectra of neat PEG-THFF overlaps with the OH-deformation vibration. The C—O stretching vibration in binary and cyclic ethers appears within the range between about 1118 cm$^{-1}$ to about 1128 cm$^{-1}$ and at about 1074 cm$^{-1}$, respectively.

Example 3

TGA Characterization of SWNT-PEG-THFF

The loading of the PEG-THFF oligomer in the functionalized material was estimated by TGA analysis. The TGA data was recorded using a Pyris 1 TGA Thermogravimetric Analyzer (Perkin-Elmer Instruments) with a heating rate of about 5° C./min in air. Because the attached functionalities are free of metal, the amount of carbon nanotubes in the material can be calculated from the metal content estimated by the TGA analysis of the starting SWNT-COOH material and the functionalized SWNTs.

Figures 5A, 5B:
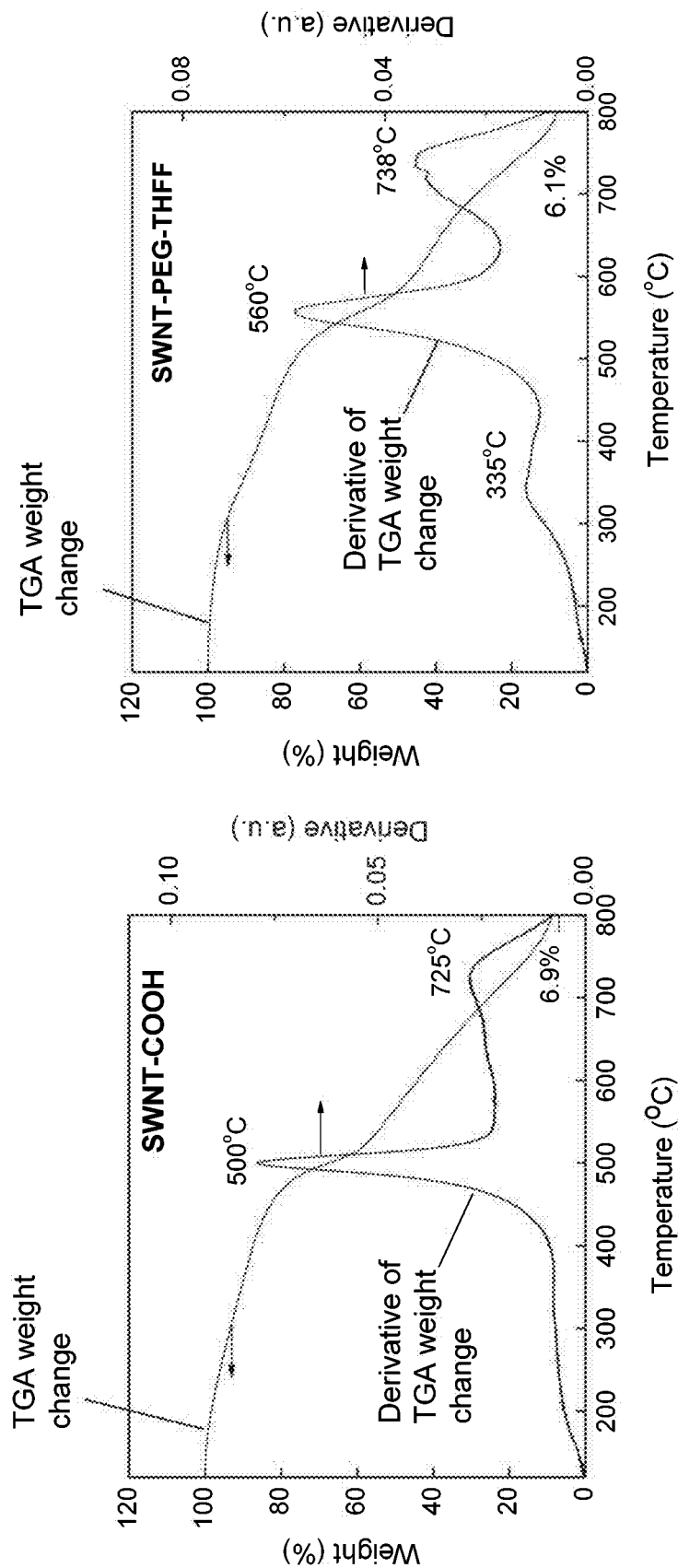
FIGS. 5A-5B are plots of weight change versus temperature and the derivative of weight change versus temperature acquired from thermogravimetric analysis (TGA) of embodiments of an SWNT-COOH starting material (5A) and SWNT-PEG-THFF (5B) taken in air at a heating rate of about 5° C./min. The residues from the TGA, in the form of metal oxides, are about 6.9 wt. % for SWNT-COOH and about 6.1 wt. % for SWNT-PEG-THFF, corresponding to metal contents of about 5.4 wt. % SWNT-COOH and about 4.8 wt. % SWNT-PEG-THFF.

In one embodiment, the SWNT-PEG-THFF material contains about 88 wt. % SWNTs and about 12 wt. % PEG-THFF, as estimated from the TGA data, which are illustrated in FIGS. 5A-5B. The residues from the TGA, in the form of metal oxides, are about 6.9 wt. % for SWNT-COOH (FIG. 5A) and about 6.1 wt. % for SWNT-PEG-THFF (FIG. 5B), corresponding to metal contents of about 5.4 wt. % SWNT-COOH and about 4.8 wt. % SWNT-PEG-THFF. Thus, the SWNT loading in the SWNT-PEG-THFF product is calculated as approximately (6.1/6.9)×100=88%.

Example 4

IR-Characterization SWNT Loading

The loading of SWNTs in the SWNT-PEG and SWNT-PEG-THFF materials can be also estimated using solution phase near-IR (NIR) spectroscopy in conjunction with applying the Beer's law:

$$A=\epsilon Cl$$

where A is the absorbance at a specific wavelength, $\epsilon$ is the extinction coefficient of the material, C is the concentration of the dispersions, and l is the cell path length.

About 5 mg of the SWNT-PEG-THFF material was dispersed by ultrasonication in about 100 mL of distilled water to form a dispersion having a SWNT-PEG-THFF concentration of about 0.05 g/L. This dispersion was used for the preparation of a series of standard solutions having concentrations of about 0.005 g/L, about 0.0125 g/L, and about 0.025 g/L. Solution phase NIR spectra were measured at about ambient temperature within the frequency range between about 7000 cm$^{-1}$ to about 30000 cm$^{-1}$.

Figure 6B:
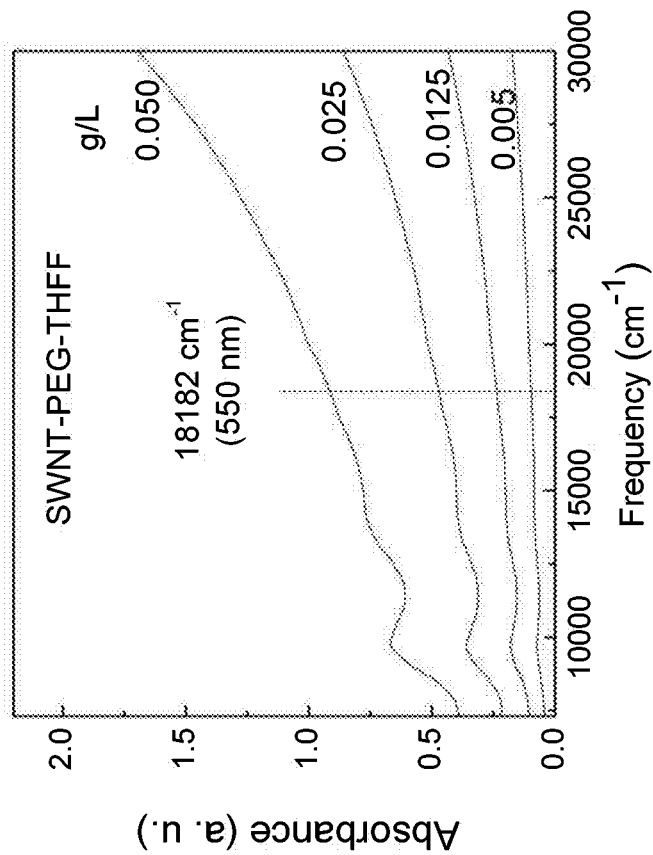
FIGS. 6A-6B are plots of absorbance versus frequency acquired from near-infrared (NIR) spectroscopy of embodiments of aqueous dispersions of: (6A) SWNT-COOH and (6B) SWNT-PEG-THFF.
Figure 6A:
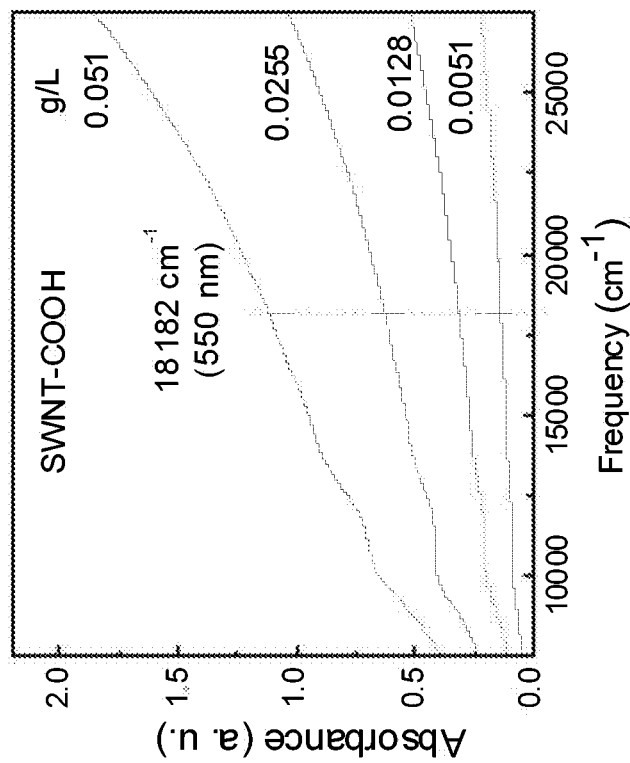
Figure 6D:
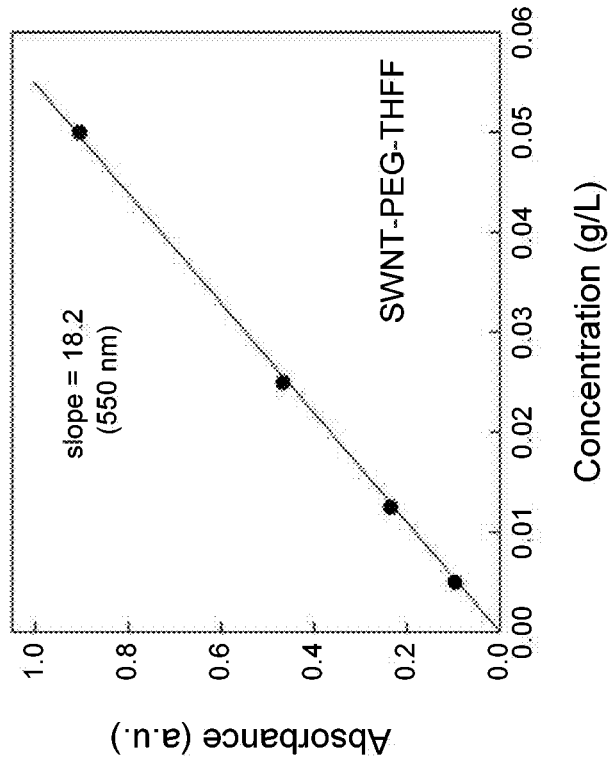
FIGS. 6C-6D are plots of absorbance versus concentration acquired from near-infrared (MR) spectroscopy of embodiments of aqueous dispersions of: SWNT-COOH (C) and SWNT-PEG-THFF (D) at about 18182 $cm^{-1}$ (550 nm)
Figure 6C:
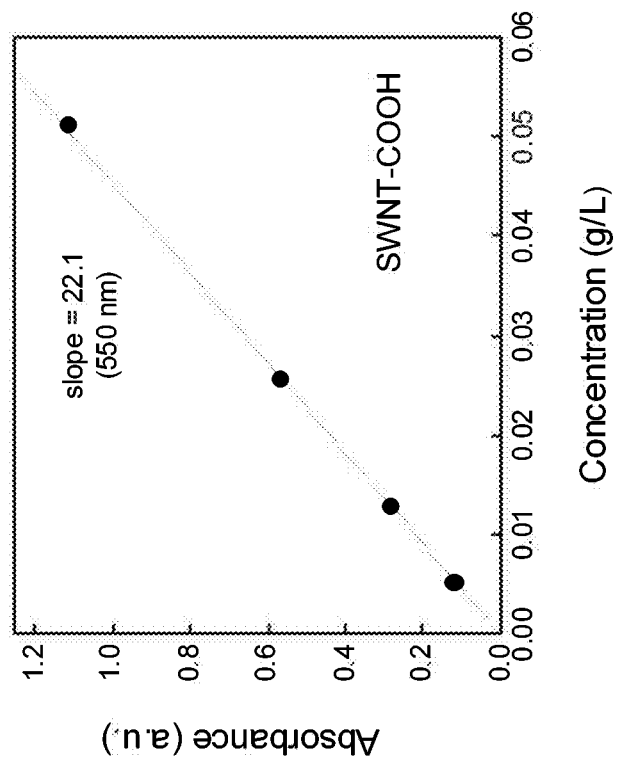

The plots of absorbance vs. frequency for a cell having a unit path length, about 1 cm, are illustrated in FIGS. 6A, 6B, while the corresponding plots of absorbance at about 18182 cm$^{-1}$ (550 nm) vs. concentration are illustrated in FIGS. 6C, 6D. The extinction coefficient is obtained from the slope of the concentration plots.

The absorbance vs. concentration measurements at about 550 nm (18182 cm$^{-1}$) provide extinction coefficients of about 22.1 for SWNT-COOH, and about 18.2 L/g cm for SWNT-PEG-THFF. After correction of the mass for the metal content, extinction coefficients of about 23.3 L/g and about 19.2 L/g cm are respectively estimated for SWNT-COOH and SWNT-PEG-THFF.

Based on these extinction coefficients the calculated SWNT content in the SWNT-PEG-THFF graft copolymer is about 82% ([19.2/23.3]×100=82%), which is close to the value estimated from the TGA data. Further assuming the molecular weight of PEG-THFF to be about 200, the fraction of carbon atoms in the SWNTs that participate in covalent bond formation with PEG-THFF is estimated to be about (18/200)/(82/12)100=1.3 mol %.

Example 5

Characterization of Carboxylic Acid Groups in SWNT-COOH by Titration

The loading fraction of PEG-THFF oligomer in the graft co-polymer depends on the concentration of carboxylic acid groups in the starting SWNT material (SWNT-COOH) and the degree to which the reaction proceeds to completion. As such, acid-base titration experiments were further performed to measure the concentration of carboxylic acid groups in the SWNT-COOH starting material.

For these experiments, the SWNT-COOH starting material was dried at about 100° C. for approximately 2 h. About 100.3 mg SWNT-COOH was immersed in approximately 25 mL of aqueous sodium bicarbonate (NaHCO$_3$, about 0.05006 N) and stirred under argon for about 48 hours. The conjugate base of the SWNT-COOH material was then filtered (membrane of approximately 0.4 μm) and washed with DDI water to remove unreacted NaHCO$_3$. The formed conjugate base salt (SWNT-COO$^-$Na$^+$) was dried at about 120° C. to obtain approximately 95.7 mg of solid, which was dispersed in about 25 mL of approximately 0.05N HCl solution by stirring under argon for about 48 h. The material was then filtered, washed with distilled water and the filtrate titrated with an approximately 0.05N aqueous solution of NaOH. About 22.99 mL of base was required to substantially neutralize the solution, which gives a molar concentration of about 1.3% carboxylic acid groups. This value is consistent with the fraction of carbon atoms in the SWNTs that participate in covalent bond formation with PEG-THFF estimated from the NIR data as described in Example 5.

From the forgoing, it may be observed that there is good correlation between the carboxylic acid groups in SWNT-COOH estimated by titration and the C-atoms participating in bonding with PEG-THFF estimated by NIR. Thus, it may be concluded that embodiments of the presently disclosed synthetic procedure allow for a more complete reaction between the carboxylic groups in the SWNTs and the PEG oligomer, as compared to the SWNT-PEG graft co-polymer reported in the literature, in which the concentration of PEG-moieties in the functionalized SWNT material was about 1 mol %. (See, e.g., Zhao, B.; Hu, H.; Perea, D.; Haddon, R. C., Synthesis and Characterization of Water Soluble Single-Walled Carbon Nanotube Graft Copolymers. *J. Am. Chem. Soc.* 2005, 127, 8197-8203), the entirety of which is incorporated by reference.

Example 6

Solubility of SWNT-PEG-THFF in Water

The solubility of the SWNT-PEG-THFF in water was examined by a procedure reported in the literature (See, e.g., Zhao, B.; Hu, H; Bhowmik, P; Itkis, M. E.; and Haddon, R. C., Synthesis and Characterization of Water Soluble Single-Walled Carbon Nanotube Graft Copolymers, *J. Am. Chem. Soc.*, 2005, 127, 8197-8203.)

Briefly, saturated solutions of the SWNT-PEG-THFF were prepared by dispersing the SWNT-PEG-THFF material in distilled water by ultrasonication for a time duration within the range between about 2 h to about 20 h and diluted to provide samples for NIR analysis. By using the extinction coefficient at the wavelength of interest, the solubility was estimated. SWNT-PEG-THFF forms stable aqueous dispersions at concentrations within the range between about 0.1 g/L to about 10 g/L. In alternative embodiments, the SWNT-PEG-THFF may be dispersed in solvents comprising, methanol, ethanol, or isopropyl alcohol.

In one embodiment, about 100 mg of the SWNT-PEG-THFF material was dispersed in about 10 mL distilled water by ultrasonication for about 4 h and left to stand overnight. An aliquot of about 50 μL was diluted to about 25 mL and the concentration of the solution was estimated from the absorption intensity at about 550 nm (about 18182 cm$^{-1}$).

By using the extinction coefficient at 550 nm about 19.2 L/g cm, the solubility of the SWNT-PEG-THFF graft copolymer in water, was estimated to be about 9 g/L. The solubility of SWNT-PEG-THFF in water was significantly higher than that of SWNT-PEG (MW$_{PEG}$ of about 600), which forms stable dispersions at concentrations of about 6 g/L. (See, e.g., Zhao, B.; Hu, H.; Perea, D.; Haddon, R. C., Synthesis and Characterization of Water Soluble Single-Walled Carbon Nanotube Graft Copolymers. *J. Am. Chem. Soc.* 2005, 127, 8197-8203.)

Example 7

Atomic Force Microscopy (AFM) Characterization of SWNT-PEG-THFF

Samples of the SWNT-PEG-THFF material were prepared for AFM characterization. AFM samples of the materials were prepared from diluted aqueous dispersions by ultrasonication. These diluted dispersions were placed on mica substrates and images were measured using a Digital Instruments Nanoscope IIIA in a tapping mode.

In one aspect, the AFM characterization was performed to identify whether the unreacted PEG-THFF oligomer was substantially present in the final product. In another aspect, the AFM characterization enabled determination of whether the average length and diameter of the SWNT-PEG-THFF present in the aqueous dispersions was affected by the dispersion procedure. As discussed below, it is observed that the average length and diameter of the SWNT-PEG-THFF present in the aqueous dispersions was affected by the dispersion procedure.

In a first dispersion experiment, about 0.1 mg of SWNT-PEG-THFF was dispersed in about 5 mL of distilled water by ultrasonication of SWNT-PEG-THFF for time durations within the range between about 2 h to about 20 h. Ultrasonication was performed with a bath sonicator at a sonic power of about 270 W. Homogeneous dispersions, without visual aggregates, were obtained. About a drop of the dispersion was placed on a mica substrate and observed in AFM tapping mode. Statistical analysis of the AFM data revealed that the nanotubes were present as bundles (FIG. 7A), with an average diameter of about 5 nm and average length of about 500 nm (FIGS. 7B, 7C), which is comparable to the results obtained on other water soluble materials, such as the SWNT-PEG graft copolymer (PEG, MW approximately 600) and SWNT-PABS.

In a second dispersion experiment, a dispersion of SWNT-PEG-THFF in water was prepared by ultrasonication and high-shear mixing. About 10 mg of SWNT-PEG-THFF was dispersed in about 10 mL of distilled water by ultrasonication using a bath sonicator with a sonic power of about 270 W for a time duration within the range between about 2 h to about 20 h. The ultrasonication was followed by high-shear mixing at a motor speed of about 5,000 to 30,000 rpm (Fisher TissueMiser homogenizer) for a time duration within the range between about 30 min to 2 h to obtain a homogeneous, viscous dispersion.

A Ubbelohde capillary viscometer was used to measure the viscosity of aqueous dispersions of SWNT-PEG-THFF. The viscosity of dispersions with concentration of about 5 g/L, prepared by sonication for about 20 h and high-shear mixing for about 1 h, was about 285 cSt. Using ultrasonication or high-shear mixing as separate techniques for dispersion of SWNT-PEG-THFF in water resulted in dispersions with lower viscosity. The viscosity of SWNT-PEG-THFF dispersions with concentration of about 5 g/L, prepared by sonication for about 20 h, was about 3.3 cSt and the dispersions prepared by high-shear mixing for about 1 h had viscosity of about 1.5 cSt.

About 1 mg of the dispersion was diluted with about 5 mL water for AFM analysis. A drop of the dispersion was placed on a mica substrate and observed using AFM in a tapping mode. The AFM images, shown in FIG. 8A, show that a large fraction of the SWNTs are unbundled and exist as individual nanotubes. The average diameter of SWNT-PEG-THFF dispersed by this procedure is about 1.5 nm and the average length is about 300 nm as illustrated in FIGS. 8B, 8C.

In summary, embodiments of the present disclosure illustrate synthetic routes for novel CNT-PEG derivatives, such as SWNT-PEG-THFF, with very high solubility in water. As the PEG oligomer covalently attached to the CNTs is short (MW of about 200), the SWNT-PEG-THFF graft copolymer is more than about 80 wt. % SWNTs. Despite the high SWNT loading, though, the material forms stable dispersions in water at high concentrations, about 9 g/L. The functionalized SWNTs may further be efficiently unbundled by a combination of ultrasonication and high-shear mixing in aqueous media, affording dispersions of very high viscosity.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. A method of forming water-soluble carbon nanotubes (CNTs), comprising:
   providing carbon nanotubes (CNTs) functionalized with carboxylic acid (CNT-COOH);
   reacting the carboxylic acid functionalized carbon nanotubes (CNT-COOH) with a reactant to form an intermediate reaction product comprising one of:
   carbon nanotubes functionalized with COCl (CNT-COCl); and
   carbon nanotubes functionalized with a group of the form

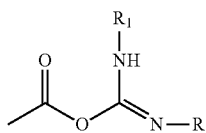

wherein R and $R_1$ are selected from phenyl, $C_3H_7$, $C_3H_6N(CH_3)_2$, and $C_2H_5$;

reacting the intermediate product with a mono-terminated, protected-polyethylene glycol (PEG) oligomer to form a carbon nanotube functionalized with the mono-terminated, protected PEG oligomer (CNT-PEG-T).

2. The method of claim 1, wherein the carbon nanotubes comprise one or more of single-walled carbon nanotubes (SWNTs), double-walled carbon nanotubes (DWNTs), few walled carbon nanotubes (FWNTs), and multi-walled carbon nanotubes (MWNTs).

3. The method of claim 1, wherein the intermediate reaction product comprises carbon nanotubes functionalized with COCl (CNT-COCl) and the reactant comprises at least one of oxalyl chloride, thionyl chloride, phosphorus trichloride, and phosphorus pentachloride.

4. The method of claim 1, wherein the intermediate reaction product comprises carbon nanotubes functionalized with a group of the form

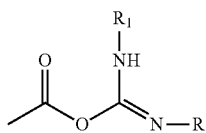

where $R=R_1=$

or $C_3H_7$ or $R=C_3H_6N(CH_3)_2$ and $R_1=C_2H_5$ and the reactant comprises at least one of N,N'-dicyclohexylcarbodiimide (DCC), N,N'-diisopropylcarbodiimide (DIC), and 1-ethyl-3-(3-dimethylaminopropyl)carbodiimide (EDC).

5. The method of claim 1, wherein reacting the intermediate product with CNT-PEG-T comprises heating the combination of the intermediate product and CNT-PEG-T to a temperature within the range between about 100° C. to about 130° C. for a time duration within the range between about 1 h to about 10 days.

6. The method of claim 1, wherein the terminal group of the mono-terminated, protected-PEG oligomer comprises one of tetrahydrofurfuryl (THFF), alkyl-tetrahydrofurfuryl, alkyl-vinyl, alkyl, alkene, and aryl functional groups.

7. The method of claim 6, wherein the mono-terminated, protected-polyethylene glycol (PEG) oligomer comprises a THFF terminal group and possesses a molecular weight of about 200 or higher.

8. The method of claim 1, wherein the carboxylic acid groups of the CNTs are covalently functionalized with the PEG oligomer during reaction of the intermediate product with mono-terminated, protected-polyethylene glycol (PEG) oligomer.

9. The method of claim 1, wherein the loading of CNTs within the CNT-PEG-T exceeds about 50 wt. %.

10. The method of claim 1, further comprising dispersing the CNT-PEG-T in a solvent comprising at least one of water, methanol, ethanol, and isopropyl alcohol.

11. A solution, comprising the CNT-PEG-T formed according to the method of claim 1 dissolved in water, wherein the concentration of CNT-PEG-T within the solution is within the range between about 0.01 g/L to about 10.0 g/L.

12. A water-soluble carbon nanotube, comprising:
a carbon nanotube functionalized with a mono-terminated, protected-polyethylene glycol (CNT-PEG-T).

13. The water-soluble carbon nanotubes of claim 12, wherein the terminal group of mono-terminated, protected-polyethylene glycol (PEG) oligomer comprises one of tetrahydrofurfuryl (THFF), alkyl-tetrahydrofurfuryl, alkyl-vinyl, alkyl, alkene, and aryl functional groups.

14. The water soluble carbon nanotube of claim 12, wherein the mono-terminated, protected-polyethylene glycol (PEG) oligomer comprises THFF-terminated PEG.

15. The water soluble carbon nanotube of claim 14, wherein the THFF-terminated PEG possesses a molecular weight of 200 or higher.

16. The water soluble carbon nanotube of claim 13, wherein the loading of carbon nanotubes within the carbon nanotube functionalized with the mono-terminated, protected PEG oligomer exceeds about 50 wt. %.

17. A water-soluble carbon nanotube consisting of the structure:

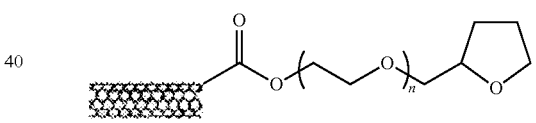

wherein n is between 2 to 20 and represents a carbon nanotube.

18. The water-soluble carbon nanotube of claim 17, wherein the loading of CNTs within structure exceeds about 50 wt. %.

19. The water-soluble carbon nanotube of claim 17, wherein the carbon nanotube comprises single-walled carbon nanotubes.

20. A solution comprising the structure of claim 17 dissolved in water, wherein the concentration of the structure within the solution is within the range between about 0.01 g/L to about 10.0 g/L.

* * * * *